(12) United States Patent
Frank

(10) Patent No.: US 7,998,152 B2
(45) Date of Patent: Aug. 16, 2011

(54) IMPLANTABLE PROSTHESIS FOR PERIAREOLAR MASTOPEXY

(76) Inventor: Robert E. Frank, Chicago, IL (US)

( * ) Notice: Subject to any disclaimer, the term of this patent is extended or adjusted under 35 U.S.C. 154(b) by 631 days.

(21) Appl. No.: 11/614,343

(22) Filed: Dec. 21, 2006

(65) Prior Publication Data
US 2008/0154366 A1 Jun. 26, 2008

(51) Int. Cl.
*A61B 17/08* (2006.01)
*A61F 2/12* (2006.01)

(52) U.S. Cl. .......... 606/151; 623/8

(58) Field of Classification Search ....... 623/8; 606/151
See application file for complete search history.

(56) References Cited

U.S. PATENT DOCUMENTS

| | | | |
|---|---|---|---|
| 3,665,520 A * | 5/1972 | Perras et al. ................. 623/8 |
| 4,372,293 A | 2/1983 | Vijil-Rosales | |
| 4,840,629 A * | 6/1989 | Bustos ........................ 623/8 |
| 5,290,217 A * | 3/1994 | Campos ...................... 600/37 |
| 5,456,714 A * | 10/1995 | Owen ......................... 623/1.31 |
| 5,584,884 A * | 12/1996 | Pignataro ................... 623/8 |
| 5,634,931 A * | 6/1997 | Kugel ......................... 606/151 |
| 5,676,161 A | 10/1997 | Breiner | |
| 5,765,567 A * | 6/1998 | Knowlton ................... 128/898 |
| 5,814,005 A * | 9/1998 | Barra et al. ................ 604/8 |
| 5,937,863 A * | 8/1999 | Knowlton ................... 128/898 |
| 6,210,439 B1 * | 4/2001 | Firmin et al. ............... 623/8 |
| 6,267,772 B1 * | 7/2001 | Mulhauser et al. ......... 606/151 |
| 6,436,030 B2 * | 8/2002 | Rehil ........................... 600/37 |
| 6,464,726 B1 | 10/2002 | Heljenek | |
| 6,485,503 B2 | 11/2002 | Jacobs et al. | |
| 6,790,213 B2 * | 9/2004 | Cherok et al. ............. 606/151 |
| 7,081,135 B2 | 7/2006 | Smith et al. | |
| 7,413,569 B2 * | 8/2008 | Sogaard-Andersen ....... 606/151 |
| 7,476,249 B2 * | 1/2009 | Frank ........................... 623/8 |
| 7,651,510 B2 * | 1/2010 | Bolduc et al. .............. 606/153 |
| 7,837,613 B2 * | 11/2010 | Lashinski et al. ........... 600/37 |
| 7,875,074 B2 * | 1/2011 | Chen et al. .................. 623/8 |
| 2004/0010275 A1 * | 1/2004 | Jacobs et al. ............... 606/153 |
| 2004/0249457 A1 * | 12/2004 | Smith et al. ................ 623/7 |
| 2005/0096499 A1 * | 5/2005 | Li et al. ....................... 600/37 |
| 2006/0036266 A1 * | 2/2006 | Sulamanidze et al. ....... 606/151 |

(Continued)

FOREIGN PATENT DOCUMENTS
FR 2682284 A1 * 4/1993

OTHER PUBLICATIONS

Coapt Systems, Inc., brochure, "Endotine for All Brow and Forehead Lift Procedures", 2005, 7 pages.

(Continued)

*Primary Examiner* — David Isabella
*Assistant Examiner* — Andrew Iwamaye
(74) *Attorney, Agent, or Firm* — Leydig, Voit & Mayer, Ltd.

(57) ABSTRACT

An implantable prosthesis for use in periareolar mastopexy. The prosthesis may constructed of a prosthetic or biological mesh material, or a biodegradable/resorbable material, and may be either annular or frusto-conical in shape. An aperture of the prosthesis is sized to surround an areola upon implantation. The prosthesis may include a plurality of teeth, extending outwardly from a top surface of the prosthesis, and canted generally towards an apex of the prosthesis. The implantable prosthesis permits a resorbable, rather than a nonresorbable suture to be used in the periareolar mastopexy procedure.

22 Claims, 4 Drawing Sheets

U.S. PATENT DOCUMENTS

| | | |
|---|---|---|
| 2006/0036333 A1 | 2/2006 | Smith et al. |
| 2006/0161253 A1* | 7/2006 | Lesh ................................. 623/8 |
| 2007/0088434 A1* | 4/2007 | Frank ................................ 623/8 |
| 2008/0097601 A1* | 4/2008 | Codori-Hurff et al. ........... 623/8 |
| 2008/0167519 A1* | 7/2008 | St-Germain ..................... 600/37 |
| 2008/0255593 A1* | 10/2008 | St-Germain ................... 606/151 |
| 2009/0082792 A1* | 3/2009 | Koyfman et al. ............. 606/151 |
| 2009/0082864 A1* | 3/2009 | Chen et al. ......................... 623/8 |
| 2009/0125107 A1* | 5/2009 | Maxwell ........................... 623/8 |
| 2009/0198332 A1* | 8/2009 | Becker ............................... 623/8 |
| 2009/0198333 A1* | 8/2009 | Becker ............................... 623/8 |
| 2009/0254103 A1* | 10/2009 | Deutsch ........................ 606/151 |
| 2010/0023029 A1* | 1/2010 | Young ........................... 606/151 |
| 2010/0191330 A1* | 7/2010 | Lauryssen et al. ................ 623/8 |
| 2010/0217388 A1* | 8/2010 | Cohen et al. ....................... 623/8 |
| 2011/0009960 A1* | 1/2011 | Altman et al. ..................... 623/8 |
| 2011/0022171 A1* | 1/2011 | Richter et al. .................... 623/8 |
| 2011/0029077 A1* | 2/2011 | Choi .................................. 623/8 |
| 2011/0035004 A1* | 2/2011 | Maxwell ........................... 623/8 |

OTHER PUBLICATIONS

Coapt Systems, Inc., brochure, "Endotine Midface", 2005, 6 pages.
Coapt Systems, Inc., website pages, Endotine product description, www.coaptsystems.com, 9 pages, printed Nov. 29, 2006.
Lifecell Corporation, website pages, AlloDerm product, www.lifecell.com, 10 pages, printed Nov. 7, 2006.

* cited by examiner

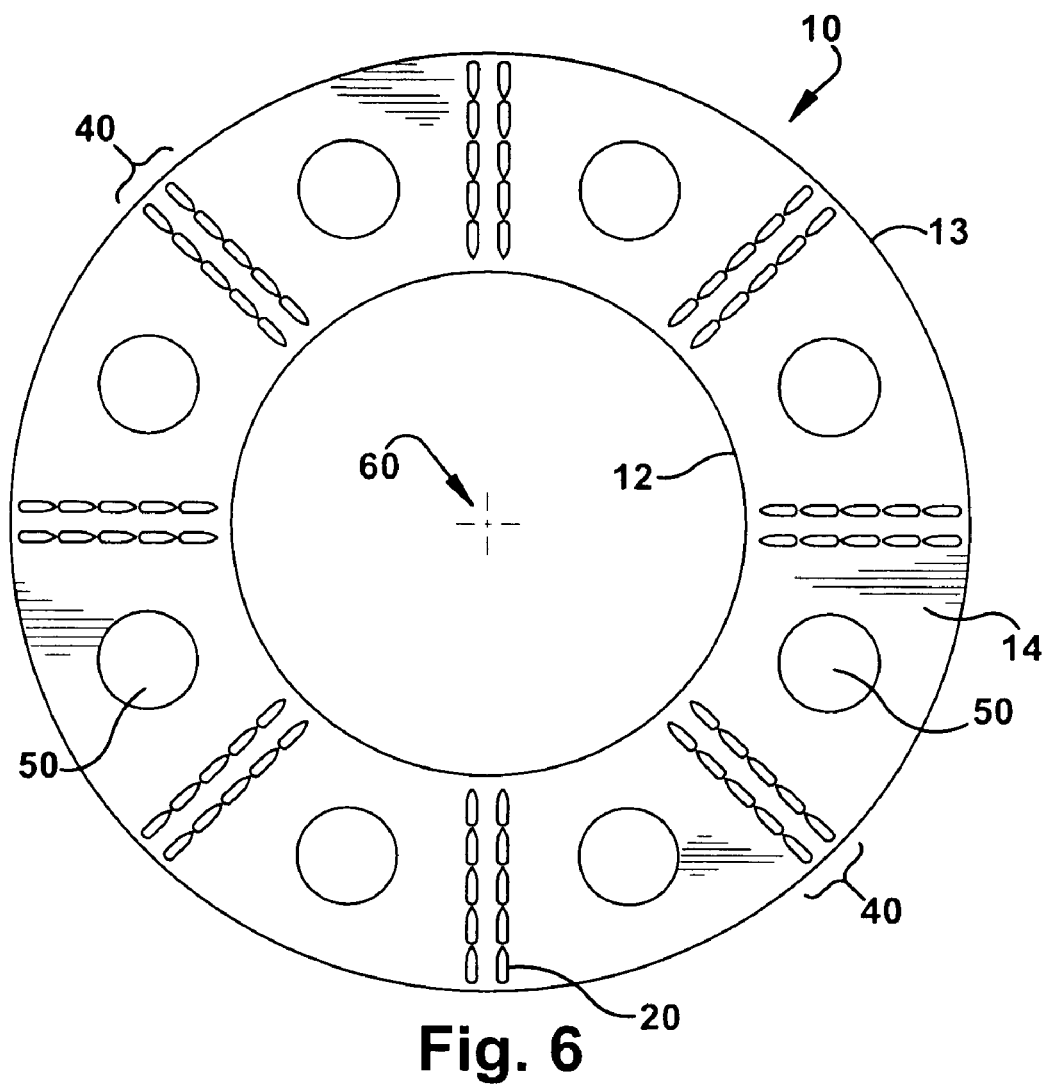
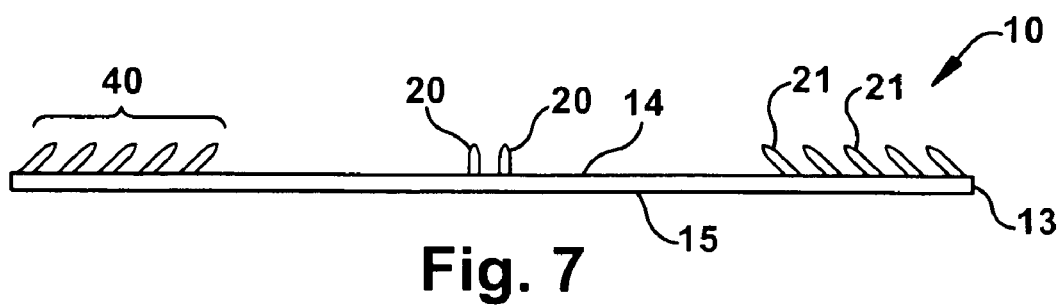

IMPLANTABLE PROSTHESIS FOR PERIAREOLAR MASTOPEXY

BACKGROUND OF INVENTION

1. Field of Invention

The present invention relates to an implantable prosthesis for performing a periareolar mastopexy and, in particular, an implantable prosthesis which eliminates the requirement of a nonresorbable suture when performing a periareolar mastopexy.

2. Description of Related Art

A mastopexy is a procedure for lifting ptotic breasts. Several variations of mastopexy are commonly performed, depending upon several factors, including the degree of ptosis. Periareolar, or Binelli mastopexy, is often recommended for patients exhibiting mild to moderate degrees of ptosis. Mastopexy may be performed as an isolated procedure, or may optionally be performed in conjunction with breast enlargement or reduction procedures.

In periareolar mastopexy, an eccentric circular region of skin surrounding the areola is removed. The skin surrounding the excised region is then drawn together using a permanent, nonresorbable pursestring suture. Traditional periareolar mastopexy has several disadvantages. First, postoperatively, the pursestring suture is palpable through the overlying skin of breast. Second, the suture may break postoperatively in one of two simultaneously treated breasts, resulting in areolar spread, wherein one areola is significantly larger than the other. Third, the suture may extrude or become visible through the skin, forming a potential nidus for infection. Fourth, the cinching of the pursestring suture can result in a flattening of the breast proximate the apex of the areola.

Accordingly, it is an object of the invention to provide an implantable prosthesis for use in periareolar mastopexy, wherein periareolar mastopexy may be performed without the need for a nonresorbable suture. It is another object of the invention to provide an implantable prosthesis for use in periareolar mastopexy, wherein the prosthesis is either not palpable through the skin, or is significantly less palpable that a nonresorbable suture. It is yet another object of the present invention to provide an implantable prosthesis for use in periareolar mastopexy, wherein postoperatively there is no nonresorbable suture which may extrude or become visible through the skin, forming a potential nidus for infection. It is still another object of the present invention to provide an implantable prosthesis for use in periareolar mastopexy, wherein there is little or no postoperative flattening of the breast proximate the apex of the areola.

BRIEF SUMMARY OF INVENTION

The present invention comprises an implantable prosthesis placed around the areola following the excision of the skin during periareolar mastopexy. Following placement of the prosthesis, a resorbable pursestring suture is employed to tack the skin surrounding the excised region to both the prosthesis and the areola.

The prosthesis is generally configured in the shape of an annulus, or "donut"-like in shape. In one embodiment, the prosthesis is substantially flat. In another embodiment, the prosthesis is frusto-conical, having the shape of the surface of a conical frustum. Preferably, the prosthesis is constructed from a sheet of material that is a porous nature to facilitate tissue in growth and secure fixation of the surrounding skin to the implantable prosthesis to the patient. In one embodiment, the prosthesis is constructed with a polypropylene substrate, with an outer surface of the prosthetic material being composed of polytetrafluoroethylene, silicone, or another suitable chemically inert material. In another preferred embodiment, the outer surface of the prosthetic material is composed of a biological mesh of human donor or porcine origin. Alternatively, the entirety of the prosthesis may be constructed of a single material, such as polytetrafluoroethylene or a biologic mesh material. In yet another preferred embodiment, the implantable prosthesis is constructed of a biodegradable, resorbable material. The implantable prosthesis may include a plurality of outwardly projecting teeth, which may be canted towards an apex region of the prosthesis.

BRIEF DESCRIPTION OF THE SEVERAL VIEW OF THE DRAWINGS

FIG. 6 is a top plan view of a third embodiment of the implantable prosthesis of the present invention;

FIG. 7 is a side elevation view of the implantable prosthesis of FIG. 6

Figure 8:
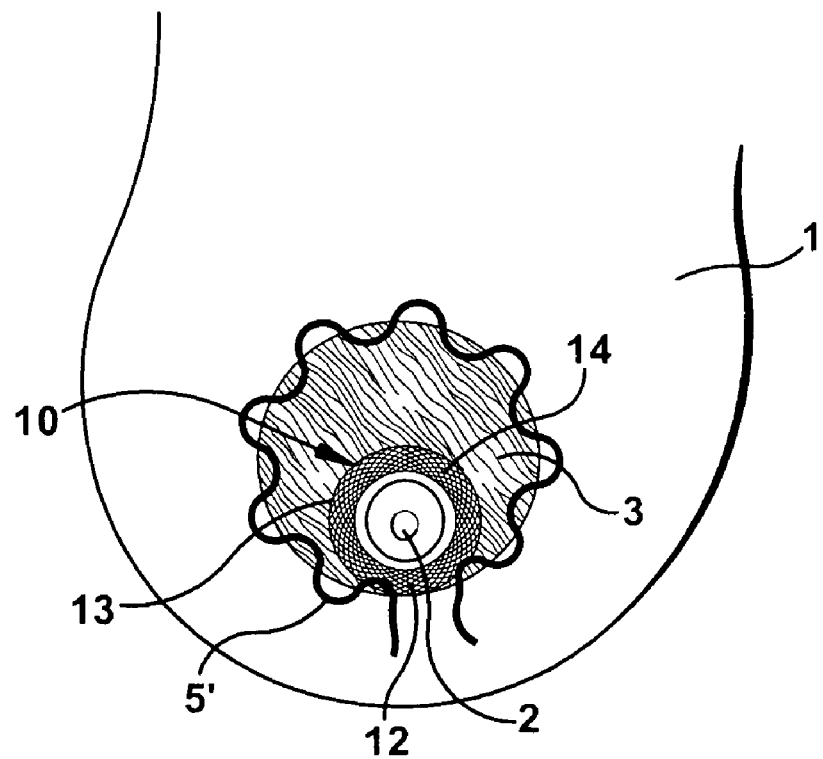
Figure 9:
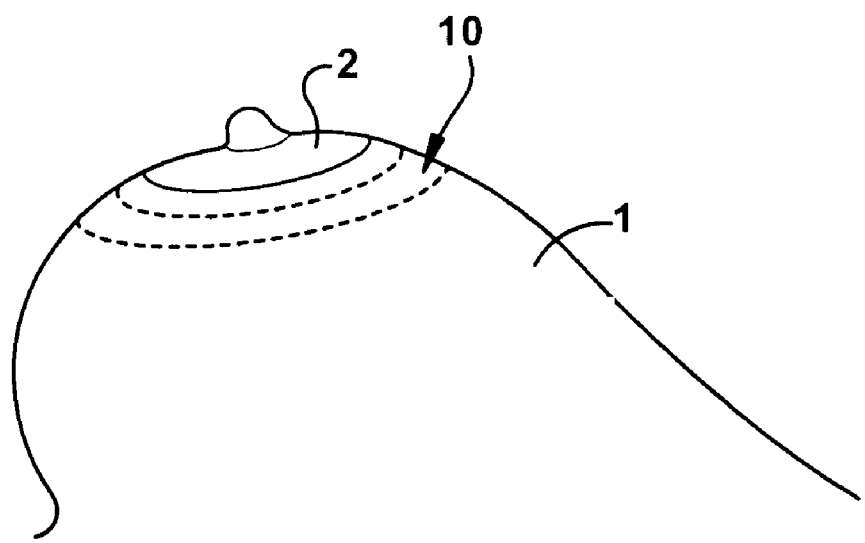

FIG. 8 is a front elevation view of a breast undergoing periareolar mastopexy in accordance with a method of the present invention and showing, in particular, the placement of the present implantable prosthesis surrounding the areola; and FIG. 9 is a side elevation view of a breast postoperative periareolar mastopexy in accordance with a method of the present invention and showing, in particular, the subcutaneous retention of the implantable prosthesis of the present invention.

DETAILED DESCRIPTION OF INVENTION

Figure 1:
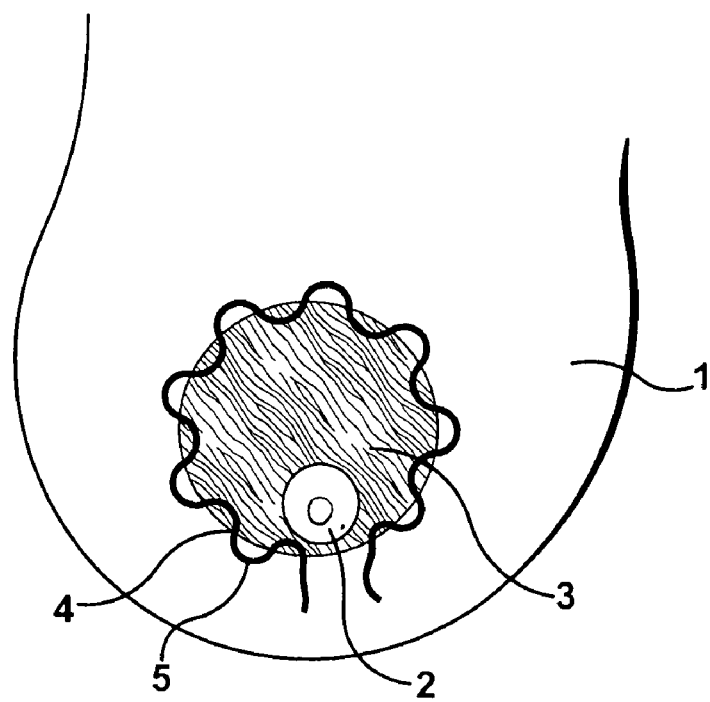
FIG. 1 is a front elevation view of a breast undergoing conventional periareolar mastopexy.
Figure 2:
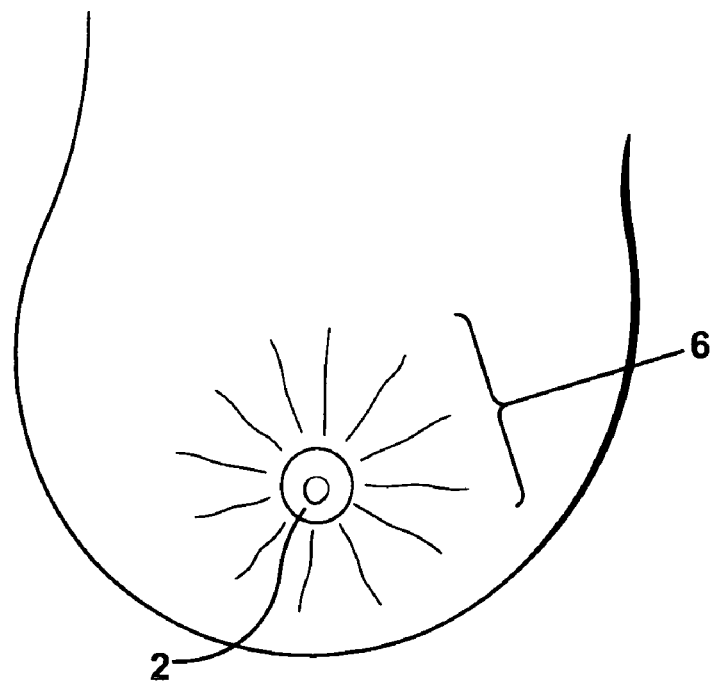
FIG. 2 is a front elevation view of a breast postoperative conventional periareolar mastopexy.

In a conventional periareolar mastopexy, as illustrated in FIG. 1, a region of skin 3 is excised from the area surrounding the areola 2 of the breast 1. As shown in FIG. 1, the excised region of skin 3 is typically in the shape of an eccentric ellipse, with a greater area of skin excised above the areola, than below it. A suture 5 is stitched in a pursestring manner proximate the edge of the skin surrounding the excised region 3. Suture 5 is typically constructed of a nonresorbable material, such as GORE-TEX, and, accordingly, is a permanent suture. The ends of suture 5 are drawn together and pulled taut, cinching the pursestring. The skin surrounding the areola is, in turn, pulled towards the areola. As a result, the areola is lifted in a cephalad direction.

The current innovation calls for the development of an implantable prosthesis in the form of an annulus, or donut-like disc of thin mesh material, which may be placed around the circumference of the areola during periareolar mastopexy. The prosthesis permits the use of resorbable, rather than nonresorbable sutures during the procedure, reducing the risk of postoperative infection. Moreover, the thin prostheses itself is not palpable, or is only minimally palpable through the skin, in contrast to the palpable nonresorbable sutures typically employed in periareolar mastopexy.

Figure 3:
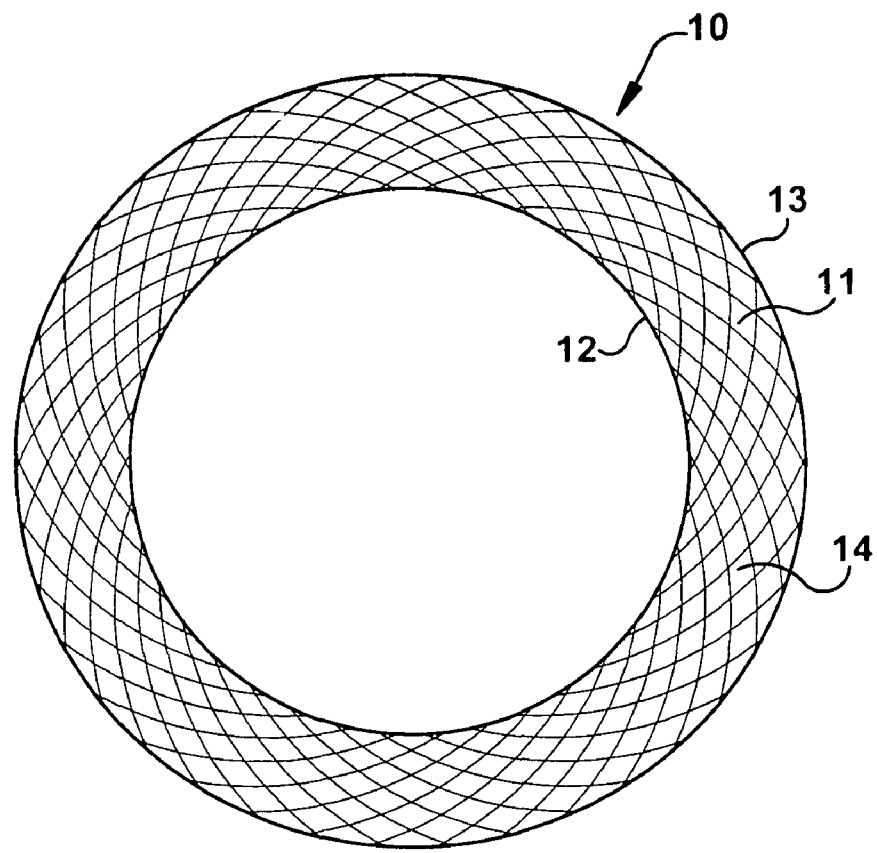
FIG. 3 is a top plan view of a first embodiment of the implantable prosthesis of the present invention.
Figure 4:
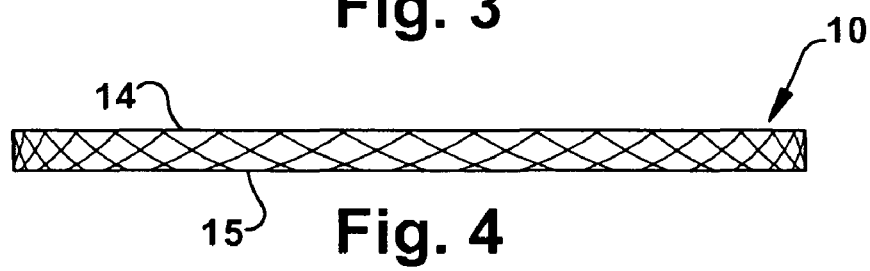
FIG. 4 is a side elevation view of the implantable prosthesis of FIG. 3.

Amongst the various embodiments of the present invention described herein, analogous or similar elements are assigned common reference numerals. A first embodiment of the implantable prosthesis of the present invention is shown in FIGS. 3 and 4 as comprising prosthesis 10, having an annular, or donut-like disc configuration. Prosthesis 10, preferably constructed of a prosthetic mesh material 11, includes inner aperture 12, outer edge 13, top surface 14 and bottom surface 15. As best seen in FIG. 4, prosthesis 10 is preferably of a relatively thin construction, to facilitate the drawing of skin surrounding the excised periareolar region over the prosthesis, as well as to reduce the risk of the prosthesis being palpable through the skin.

Figure 5:
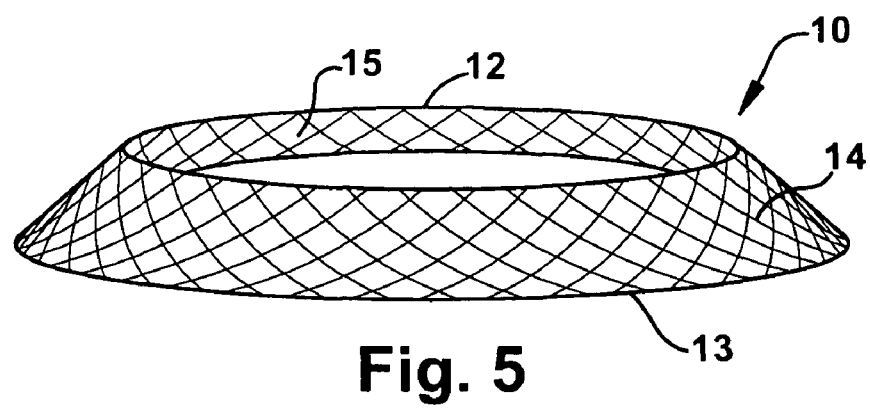
FIG. 5 is a side perspective view of a second embodiment of the implantable prosthesis of the present invention.

A second embodiment of the implantable prosthesis of the present invention is shown in FIG. 5. In this embodiment, prosthesis 10 is slightly frusto-conical in shape, being formed in the shape of a conical frustum. The slightly conical shape of this embodiment serves to minimize the flattening of the breast that can occur, particularly proximate the apex of the areola, as may occur following conventional periareolar mastopexy. In this embodiment, and as is shown in FIG. 5, top surface 14 serves as the outer surface of the conical prosthesis, and bottom surface 15 serves as the inner surface of the conical prosthesis.

The mesh material of the present implantable prosthesis may be constructed of a polypropylene mesh having pore size and density configured to promote in growth of the surrounding tissue upon placement of the implantable prosthesis within the patient. The polypropylene mesh may be covered or coated with polytetrafluoroethylene, silicone, or another suitable chemically inert material.

Alternatively, a biologic mesh may be substituted for some, or all, of the polypropylene mesh and/or the chemically inert material previously discussed. The biologic mesh typically comprises an acellular dermal matrix, comprising skin from which the epidermis, as well as antigens which may lead to tissue rejection, have been removed. The acellular matrix may be of porcine origin, or may be derived from human donor tissue, such as the ALLODERM acellular dermal matrix sold by LifeCell Corporation. A portion, or all, of the surface of a mesh of polypropylene or other suitable porous material may be covered with a biologic mesh or dermal matrix material. In this manner, the polypropylene mesh will serve to add additional framework and support for the biologic mesh material. Alternatively, a prosthesis of unitary biological mesh construction may be employed.

A third embodiment of the implantable prosthesis of the present invention is shown in FIGS. 6 and 7 as comprising prosthesis 10, again having an annular, or donut-like disc configuration. As best seen in FIG. 7, prosthesis 10 is preferably of a relatively thin construction, to facilitate the drawing of skin surrounding the excised periareolar region over the prosthesis, as well as to reduce the risk of the prosthesis being palpable through the skin.

Moreover, in this embodiment, prosthesis 10 further includes a plurality of projections in the form of teeth, barbs, prongs or tines 20, extending from top surface 14 of the prosthesis. Although teeth 20 are illustrated in FIGS. 6-7 as being generally cylindrical in individual construction, with an angled, substantially sharp pointed end 21 distal from top surface 14, teeth 20 may be configured in any of the various shaped identified in U.S. Pat. No. 6,485,503, the entire contents of which are hereby incorporated by reference. In this embodiment, teeth 20 are preferably constructed of a resorbable material 16, with the remaining, annular portion of the prosthesis being constructed of a prosthetic mesh material or a biological mesh material, as described above with respect to the embodiments of FIGS. 3-5. Teeth 20 are preferably affixed or adhered to the annular portion of the prosthesis using, for example, a suitable adhesive. Resorbable material 16 is preferably of a composition which takes weeks to months for complete resorption to occur, following implantation. In particular, resorbable material 16 may be a synthetic material such as polylactide polymer, or any of the suitable materials identified in U.S. Pat. No. 6,485,503.

As shown in FIG. 7, the annular body of prosthesis 10 is substantially thin and planar. Teeth 20 are preferably arranged in eight groups 40. Each group 40 comprises ten teeth, arranged in two parallel rows of five. As best seen in FIG. 6, each group 40 is evenly spaced at 45 degree interval radii aligned with the theoretical geometric center 60 of the prosthesis. As shown in FIG. 6, groups of teeth 40 are substantially aligned with parallel rows on either sides of 45, 90, 135, 180, 225, 270, 315, and 360 degree radials, relative to geometric center 60. Moreover, teeth 20 are all canted generally towards the geometric center 60 of the prosthesis, at an angle of approximately 45 degrees, relative to the planar top surface 14. Each tooth, or tine 20 is preferably approximately 3.18 millimeters in length, and approximately 1.0 millimeters in diameter.

As shown in FIG. 6, the annular body of the implantable prosthesis of this embodiment further includes eight apertures 50 extending through the body of the prosthesis, from top surface 14 to bottom surface 15. The eight apertures are disposed substantially evenly spaced at 45 degree interval radii aligned with the theoretical geometric center 60 of the prosthesis, and each aperture is further disposed approximately equidistantly from outer edge 13 and aperture 12. As shown in FIG. 9, apertures 50 are disposed with centers of the apertures on 22.5, 67.5, 112.5, 157.5, 202.5, 247.5, 292.5, and 337.5 degree radials, relative to geometric center 60. The purpose of apertures 50 is to create defined areas of weakness within the body portion of the implantable prosthesis. It is believed that, upon performing a periareolar mastopexy procedure using this embodiment of the present invention, as described below, these defined areas of weakness may permit the body of the implantable prosthesis to deform from a substantially planar shape to a shape approximating that of a conical frustum, upon the cinching of the resorbable pursestring suture, as described in further detail below.

Alternatively, apertures 50 may be omitted. Moreover, the annular portion of the implantable prosthesis may alternatively be fabricated to be substantially frusto-conical in shape, similar to the embodiment of FIG. 5, rather than substantially planar in shape, with teeth 20 disposed along the sloping top surface of the prosthesis and canted inwardly, again towards the center of the prosthesis. Of course, such a construction would eliminate the need for any apertures 50 to prompt the prosthesis into such a frusto-conical shape upon implantation.

The dimensions of an example implantable prosthesis 10 is an outer diameter of approximately 79.8 millimeters (as measured at outer edge 13), and an inner diameter of approximately 39.8 millimeters (as measured at aperture 12), yielding a width of the annulus, or ring of the prosthesis of approximately 40.0 millimeters (as measured along any radii emanating from geometric center 60). Moreover, the thickness of an example implantable prosthesis, between top surface 14 and bottom surface 15, is approximately 0.23 millimeter. Each aperture 50 is approximately 9.5 millimeters in diameter.

In a preferred embodiment, the dimensions of implantable prosthesis 10 are preferably sized to meet the criteria of each particular application, including the size of the patient's areola. In one embodiment of the present invention, a sheet of prosthetic material is provided in the form of a circular disc. The surgeon may remove an inner, circular region of material of sufficient area, such that the circumference of aperture 12 is sized to surround the patient's areola. The surgeon may then remove additional material from the outer edge 13 of the prosthetic material, creating an annular ring of a desired overall width. In this manner, the implantable prosthesis may be custom sized for each particular application.

Alternatively, a variety of differently sized implantable prostheses, having differently sized inner apertures 12, and/or circumferences of outer edge 13, may be provided towards accommodating anticipated anatomical variations amongst prospective patients. A surgeon may order a desired, predetermined size for a particular patient in advance, from a selection of predetermined, standard sizes of implantable prostheses made available by a manufacturer. Moreover a kit, comprising a plurality of variously sized prostheses may be supplied to the surgeon. The kit may include, for example, prostheses of varying aperture sizes, variable outer circumferences, or both (resulting, in turn, in varying width of the planar ring of material. Moreover, implantable prostheses of varying thicknesses between top edge 15 and bottom edge 14 may be supplied. For either custom-ordered or kit-supplied prostheses, the outer diameter, inner aperture diameter, or both may be varied by up to several tens of millimeters larger or smaller, relative to the exemplary dimensions described above. Moreover, the overall thickness of the prosthesis may be varied by up to several hundredths or tenths of a millimeter, either thicker or thinner, relative to the exemplary dimensions described above.

A periareolar mastopexy procedure, employing the present implantable prosthesis of any of the previously described embodiments of the present invention, is illustrated in FIG. 8. First, an eccentric ellipse of skin 3 surrounding the areola, including an enlarged region above the areola, is excised, as in a conventional periareolar mastopexy. Next, an implantable prosthesis 10 of suitable size (either a suitable predetermined size, or custom sized to fit, as discussed above) is placed, with aperture 12 surrounding the areola, and upper surface 14 placed anterior to the excised region.

Next, a pursestring suture 5' of suitable, resorbable material, is first placed, and then cinched tight to a desired diameter. When employing an implantable prosthesis of the embodiments of FIGS. 3-4 or FIG. 5, pursestring suture 5' is further used to tack the surrounding skin to the prosthesis and the areola. When employing an implantable prosthesis of FIGS. 6-7, teeth 20 serve to perform tissue fixation relative to the skin in the region anterior to the prosthesis. For this embodiment, pursestring suture 5' is cinched tight to a desired diameter to draw the skin surrounding the excised region over the prosthesis, but is not used to tack the surrounding skin to the prosthesis itself. For any of the embodiments of the implantable prosthesis of the present invention, a nonresorbable suture, rather than a resorbable suture, may be employed as the pursestring suture in the periareolar mastopexy procedure.

Postoperatively, and as shown in FIG. 9, the areola is lifted in a cephalad direction, and the prosthesis of the present invention is retained, subcutaneously in the region surrounding the areola. For the embodiments of FIGS. 3-4 and FIG. 5, the entirety of the prosthesis is retained indefinitely. For the embodiment of FIGS. 6-7, the resorbable teeth portion of the prosthesis is retained for weeks or months, until complete resorption of the teeth occurs. The annular disc portion of the prosthesis of FIGS. 6-7 is retained indefinitely.

It will be understood that modifications and variations may be effected without departing from the spirit and scope of the present invention. It will be appreciated that the present disclosure is intended as an exemplification of the invention and is not intended to limit the invention to the specific embodiments illustrated and described. The disclosure is intended to cover, by the appended claims, all such modifications as fall within the scope of the claims.

I claim:

1. An implantable prosthesis for use in periareolar mastopexy, the implantable prosthesis comprising:
   a generally annular body made from a porous material having a top surface and a bottom surface;
   a first circular aperture disposed at an approximate geometric center of the body and extending through the top and bottom surfaces, the first circular aperture being sized to surround an areola of a breast;
   a plurality of groups of tines extending from the top surface, each group of tines being arranged as a pair of generally parallel rows of tines, each row having a plurality of tines canted towards the first aperture, each group of rows being aligned with the approximate geometric center of the body;
   a plurality of second circular apertures formed in the porous material and extending from the top surface to the bottom surface and arranged such that a second aperture is disposed between each adjacent group of tines; and
   wherein the plurality of second circular apertures provide defined areas of weakness to permit the body to deform from a substantially planar shape to a shape approximating that of a conical frustum.

2. The implantable prosthesis according to claim 1, wherein the implantable prosthesis is constructed from a prosthetic mesh material.

3. The implantable prosthesis according to claim 2, wherein the prosthetic mesh material comprises polypropylene.

4. The implantable prosthesis according to claim 1, wherein the implantable prosthesis includes at least one surface of chemically inert material.

5. The implantable prosthesis according to claim 4, wherein the chemically inert material is selected from the group comprising polytetrafluoroethylene and silicone.

6. The implantable prosthesis according to claim 1, wherein the implantable prosthesis is constructed from a biological mesh material.

7. The implantable prosthesis according to claim 6, wherein the biological mesh material is of human donor origin.

8. The implantable prosthesis according to claim 6, wherein the biological mesh material is of porcine origin.

9. The implantable prosthesis according to claim 1, wherein at least one of the plurality of tines is constructed from a resorbable material.

10. The implantable prosthesis according to claim 9, wherein the resorbable material is a polyactide polymer.

11. The implantable prosthesis according to claim 1, wherein the plurality of groups of tines are spaced approximately 45 degrees apart.

12. A kit comprising:
    a plurality of implantable prostheses for use in periareolar mastopexy, each of the implantable prostheses having:
       a generally annular body made from a porous material with a top surface and a bottom surface;
       a first circular aperture disposed at an approximate geometric center of the body and extending through the top and bottom surfaces, the first circular aperture being sized to surround an areola of a breast;

an outer circumference;

a plurality of groups of tines extending from the top surface, each group of tines being arranged as a pair of generally parallel rows of tines, each row having a plurality of tines canted towards the first aperture, each group of rows being aligned with the approximate geometric center of the body;

a plurality of second circular apertures formed in the porous material and extending from the top surface to the bottom surface and arranged such that a second aperture is disposed between each adjacent group of tines; and wherein the plurality of second circular apertures provide defined areas of weakness to permit the body to deform from a substantially planar shape to a shape approximating that of a conical frustum; and at least one of the implantable prostheses in the kit differing in at least one of first aperture size, outer circumference size, and thickness, relative to another implantable prosthesis in the kit.

13. The kit according to claim 12, wherein the plurality of implantable prostheses are constructed from a prosthetic mesh material.

14. The kit according to claim 13, wherein the prosthetic mesh material comprises Polypropylene.

15. The kit according to claim 12, wherein the plurality of implantable prostheses include at least one surface of chemically inert material.

16. The kit according to claim 15, wherein the chemically inert material is selected from the group comprising polytetrafluoroethylene and silicone.

17. The kit according to claim 12, wherein the plurality of implantable prostheses are constructed from a biological mesh material.

18. The kit according to claim 17, wherein the biological mesh material is of human donor origin.

19. The kit according to claim 17, wherein the biological mesh material is of porcine origin.

20. The kit according to claim 12, wherein at least one of the plurality of tines is constructed from a resorbable material.

21. The kit according to claim 20, wherein the resorbable material is a polyactide polymer.

22. The kit according to claim 12, wherein the plurality of groups of tines are spaced approximately 45 degrees apart.

* * * * *